US010231881B2

(12) United States Patent
Vee et al.

(10) Patent No.: US 10,231,881 B2
(45) Date of Patent: Mar. 19, 2019

(54) THERAPEUTIC COMPRESSION GARMENT AND METHOD OF APPLYING THE GARMENT

(71) Applicants: Nancy Louise Vee, Madelia, MN (US); Karen Kay Gunderson, Madelia, MN (US)

(72) Inventors: Nancy Louise Vee, Madelia, MN (US); Karen Kay Gunderson, Madelia, MN (US)

(*) Notice: Subject to any disclaimer, the term of this patent is extended or adjusted under 35 U.S.C. 154(b) by 689 days.

(21) Appl. No.: 14/868,097

(22) Filed: Sep. 28, 2015

(65) Prior Publication Data

US 2016/0100988 A1    Apr. 14, 2016

Related U.S. Application Data

(60) Provisional application No. 62/061,488, filed on Oct. 8, 2014, provisional application No. 62/061,495, filed on Oct. 8, 2014.

(51) Int. Cl.
| *A61F 13/00* | (2006.01) |
| *A61F 13/08* | (2006.01) |
| *A61F 13/02* | (2006.01) |
| *A61F 13/06* | (2006.01) |

(52) U.S. Cl.
CPC .......... *A61F 13/08* (2013.01); *A61F 13/0273* (2013.01); *A61F 13/061* (2013.01)

(58) Field of Classification Search
CPC ..... A61F 13/08; A61F 13/085; A61F 13/0276
USPC .............................................. 602/60, 62, 63
See application file for complete search history.

(56) References Cited

U.S. PATENT DOCUMENTS

| 4,205,667 | A | * | 6/1980 | Gaylord, Jr. | ............ A61F 5/055 128/DIG. 23 |
| 4,374,518 | A | | 2/1983 | Villanueva | |
| 4,827,915 | A | * | 5/1989 | Gorsen | .................... A61F 5/055 128/DIG. 23 |
| 5,036,838 | A | * | 8/1991 | Sherman | ................. A61F 13/06 128/DIG. 15 |
| 5,139,476 | A | * | 8/1992 | Peters | .................... A61F 5/0106 602/23 |
| 5,338,290 | A | * | 8/1994 | Aboud | .................... A61F 13/06 602/62 |
| D397,222 | S | | 8/1998 | Humensky | |
| 5,916,183 | A | | 6/1999 | Reid | |
| 6,048,326 | A | * | 4/2000 | Davis | .................... A61F 5/0106 602/26 |
| 6,179,796 | B1 | | 1/2001 | Waldridge | |

(Continued)

*Primary Examiner* — Kim M Lewis
(74) *Attorney, Agent, or Firm* — Shifrin Patent Law; Dan Shifrin

(57) ABSTRACT

A therapeutic compression wrap is provided, comprising: a first front foam panel having inside and outside surfaces and configured to cover a front portion of at least part of a patient's limb; loop closure material stretched over and secured to the outside surface of the first front foam panel; a first back foam panel having inside and outside surfaces and configured to cover a back portion of the at least part of the limb; fabric stretched over and secured to the outside surface of the first back foam panel; and first hook closure material secured to side edges of the inside surface of the back foam panel, the first hook closure material matable with the loop closure material whereby the back foam panel is securable to the front foam panel.

17 Claims, 17 Drawing Sheets

(56) References Cited

U.S. PATENT DOCUMENTS

| | | | |
|---|---|---|---|
| 6,436,064 B1 | 8/2002 | Kloecker | |
| 6,852,089 B2 | 2/2005 | Kloecker | |
| 6,891,078 B1 | 5/2005 | Dillard | |
| 7,584,755 B2 | 9/2009 | Reid | |
| D649,255 S | 11/2011 | Kase | |
| 8,052,630 B2 | 11/2011 | Kloecker | |
| 8,523,794 B2 | 9/2013 | Iker | |
| 8,529,483 B2 | 9/2013 | Farrow | |
| 8,777,886 B2 * | 7/2014 | Mueller | A61F 13/085 602/61 |
| 9,033,906 B2 | 5/2015 | Nolan | |
| 2007/0179421 A1 * | 8/2007 | Farrow | A61H 9/005 602/75 |
| 2009/0275873 A1 | 11/2009 | Achtelstetter | |
| 2010/0262059 A1 * | 10/2010 | Doya | A61F 13/0273 602/53 |
| 2011/0125183 A1 * | 5/2011 | Lipshaw | A61F 13/085 606/201 |
| 2011/0245743 A1 | 10/2011 | Eddy | |
| 2015/0025424 A1 * | 1/2015 | Richardson | A61F 13/085 601/84 |
| 2016/0030267 A1 * | 2/2016 | Lipshaw | A61H 1/008 601/84 |
| 2016/0038346 A1 * | 2/2016 | Collins | A61F 13/08 602/63 |

\* cited by examiner

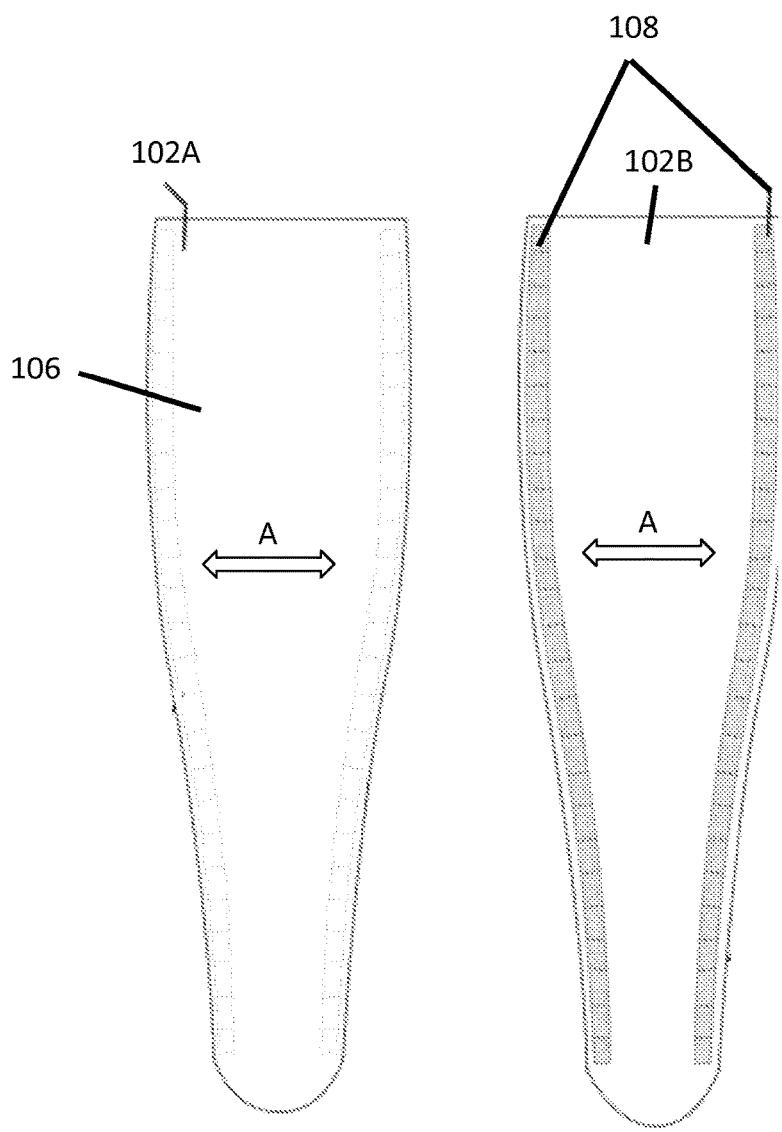

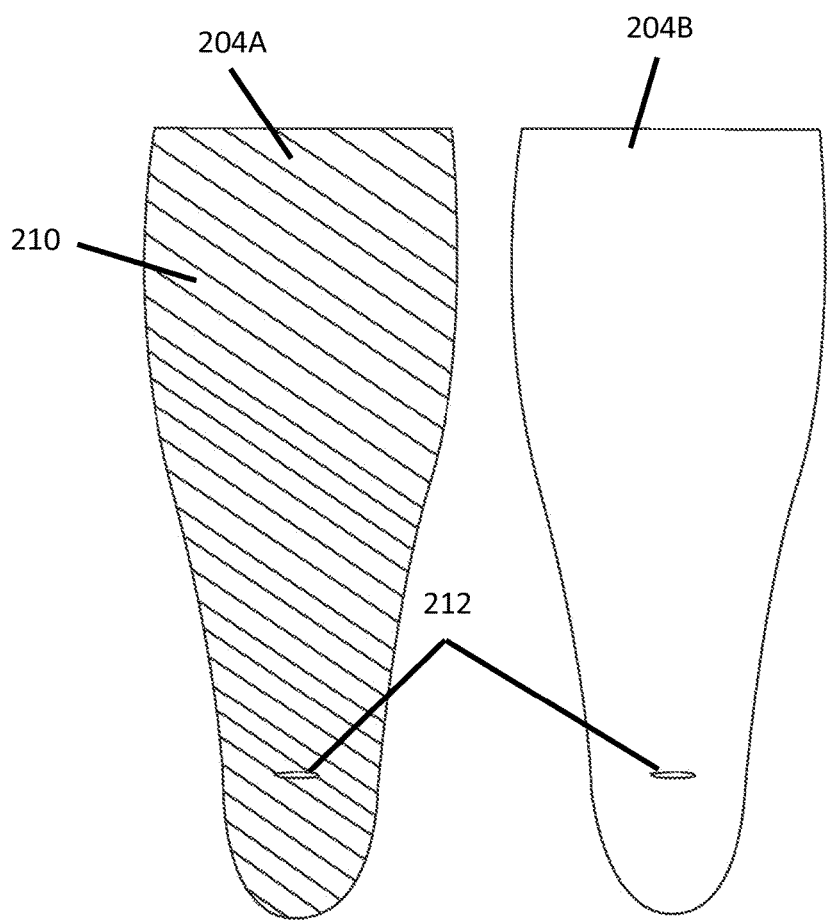

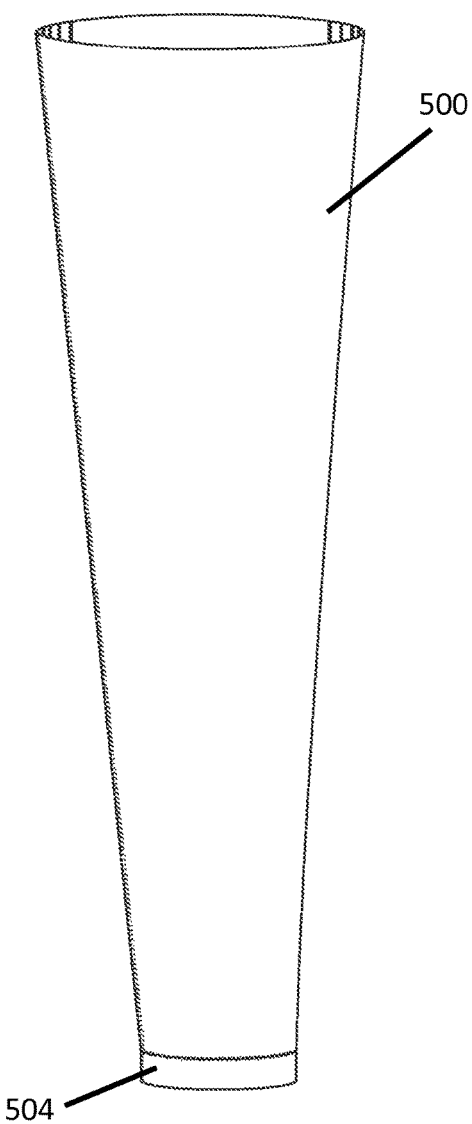
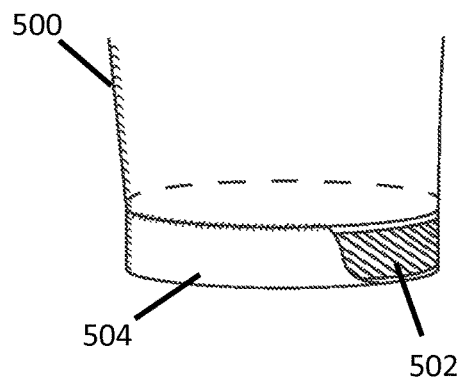
FIG. 17
FIG. 18

THERAPEUTIC COMPRESSION GARMENT AND METHOD OF APPLYING THE GARMENT

RELATED APPLICATION DATA

The present application is related to commonly-owned U.S. Provisional Application Ser. Nos. 62/061,495, entitled WICK-DRI SLEEVE/FOAM COMPRESSION WRAP, and 62/061,488, entitled SHORT AND LONG STRETCH BANDAGE/WRAP, both of which were filed on Oct. 8, 2014, and both of which are incorporated herein by reference in their entireties.

TECHNICAL FIELD

The present invention relates generally to the treatment of symptoms of fluid retention in human limbs, such as from lymphedema, and, in particular, to a therapeutic compression wrap and method of applying the wrap to a limb to reduce swelling of the limb.

BACKGROUND ART

Lymphedema is among several medical conditions that causes retention of fluid in one or more extremities of a human body. Without going into medical detail, lymphedema may be caused by a compromised lymphatic system, reducing the ability of lymphatic fluid to properly move from the extremity, such as a leg. Resulting swelling of the extremity may range from slight to severe and may impede every day activities as well as causing discomfort. Various mild to severe complications may occur if lymphedema is not treated properly.

The typical treatment for lymphedema includes the use of compression around the affected limb in an effort to move fluid from the limb towards the body. Various compression wraps are known but have numerous drawbacks, not the least of which is the time it takes to secure a compression wrap in place, often taking 45-60 minutes to secure wraps onto two limbs. In addition to being time consuming, current methods may necessitate the services of a medical professional, thereby requiring the patient to incur expenses, such as insurance co-pays, and travel time.

SUMMARY OF THE INVENTION

Embodiments of the present invention provide a therapeutic compression wrap, comprising: a first front foam panel having inside and outside surfaces and configured to cover a front portion of at least part of a patient's limb; loop closure material stretched over and secured to the outside surface of the first front foam panel; a first back foam panel having inside and outside surfaces and configured to cover a back portion of the at least part of the limb; fabric stretched over and secured to the outside surface of the first back foam panel; and first hook closure material secured to side edges of the inside surface of the back foam panel, the first hook closure material matable with the loop closure material whereby the back foam panel is securable to the front foam panel.

Embodiments of the present invention also include a method of applying a compression wrap to a patient's limb and a method of providing a therapeutic compression wrap.

BRIEF DESCRIPTION OF THE DRAWINGS

FIG. 2A illustrates the outside of the back panel of the full leg foam compression wrap of FIG. 1;

FIG. 2B illustrates the inside of the back panel of the full leg foam compression wrap of FIG. 1;

FIG. 6A illustrates the outside of the front panel of the lower leg foam compression wrap of FIG. 4;

FIG. 6B illustrates the inside of the front panel of the lower leg foam compression wrap of FIG. 4;

FIG. 17 illustrates an inner sleeve that may be worn under the foam compression wrap of FIGS. 1, 4, and 7;

FIG. 18 illustrates a lower end of the inner sleeve of FIG. 17;

DETAILED DESCRIPTION OF THE PREFERRED EMBODIMENT

The described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention can be practiced without one or more of the specific details, or with other methods, components and so forth. In other instances, well-known structures, materials, or operations are not shown or described in detail to avoid obscuring aspects of the invention.

Embodiments of the present invention provide easy to secure foam compression wraps that may be used in the treatment of Lymphedema and other related conditions. In fact, the foam compression wraps of the present invention may be secured by the patient, without requiring the services of a health care professional, onto two limbs in about 15 minutes, a considerable savings of time. As will be described, embodiments of the present invention include a full limb foam compression wrap (illustrated and described using a compression wrap for a leg as an example), a lower limb compression wrap (illustrated and described using a lower leg wrap as an example), and an upper limb compression wrap (illustrated and described using a compression wrap for a thigh as an example). Embodiments of the present invention also provide a short stretch wrap, which may be used to secure the foam compression wraps in place, and a sleeve, which may be used as a base layer under the foam compression wraps.

Figure 1:
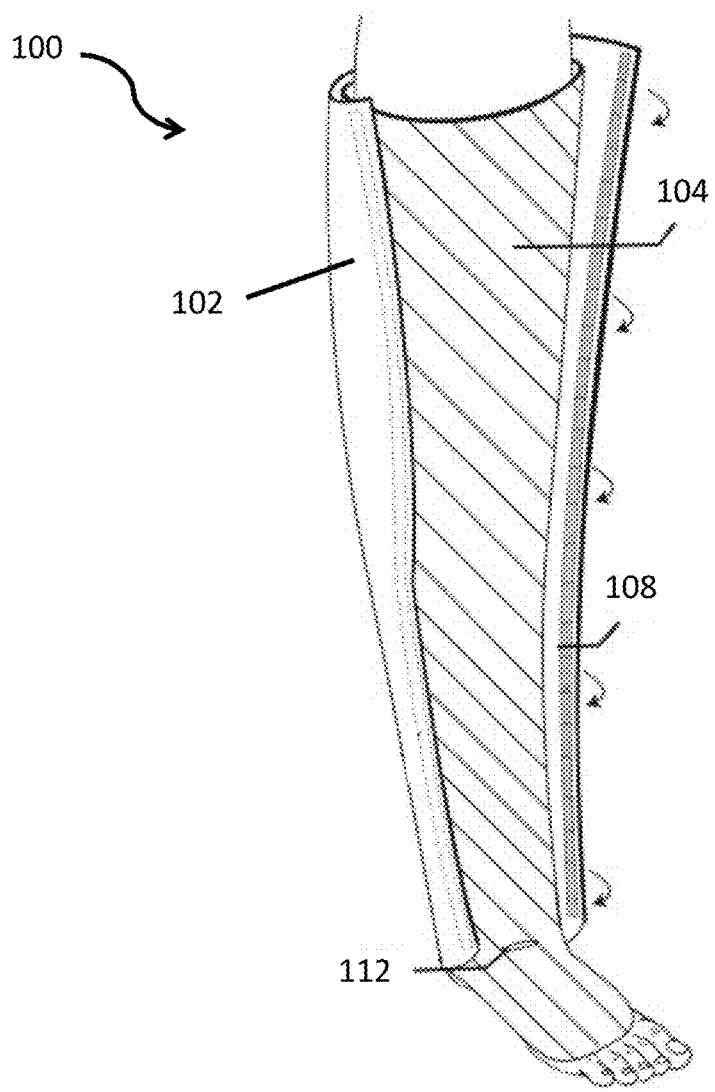
FIG. 1 illustrates a front perspective view of an embodiment of a full leg foam compression wrap of the present invention.
Figures 3A, 3B:
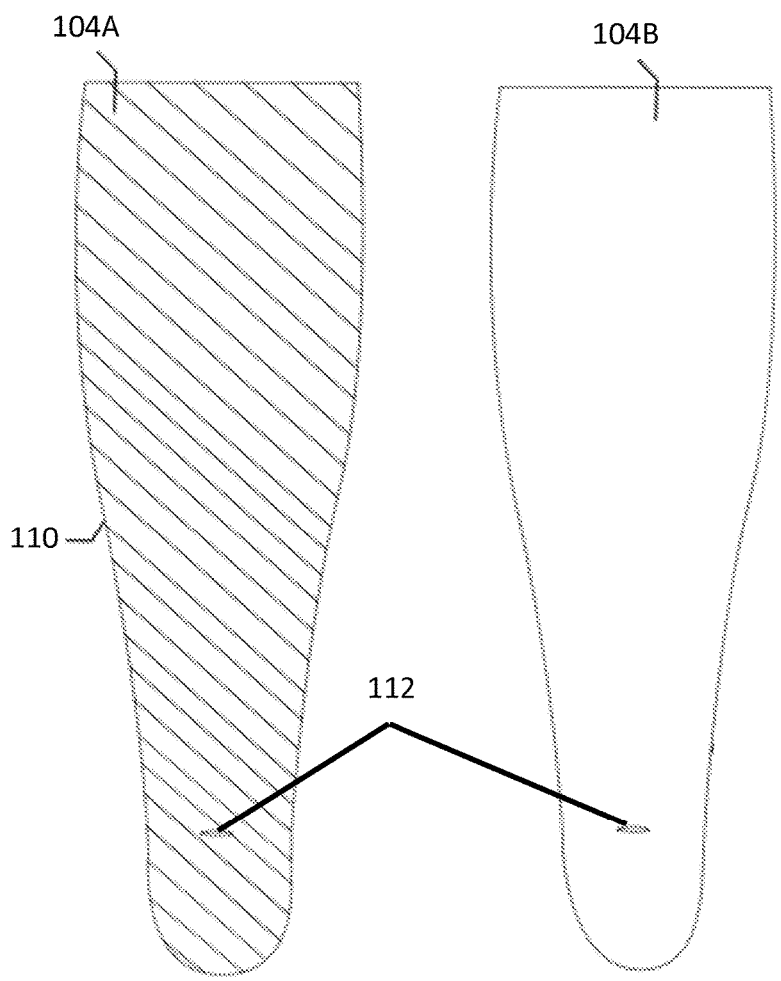
FIG. 3A illustrates the outside of the front panel of the full leg foam compression wrap of FIG. 1.
FIG. 3B illustrates the inside of the front panel of the full leg foam compression wrap of FIG. 1.
Figure 4:
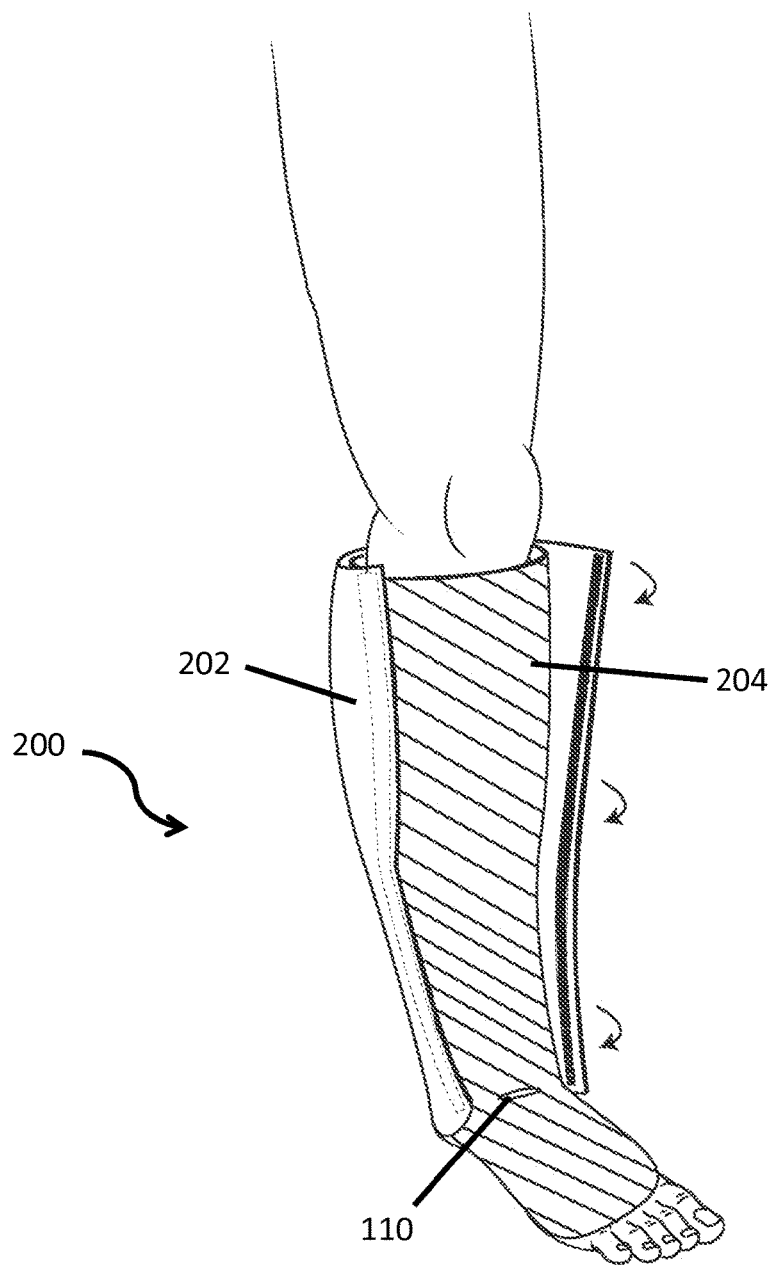
FIG. 4 illustrates a front perspective view of an embodiment of a lower leg foam compression wrap of the present invention.
Figure 21:
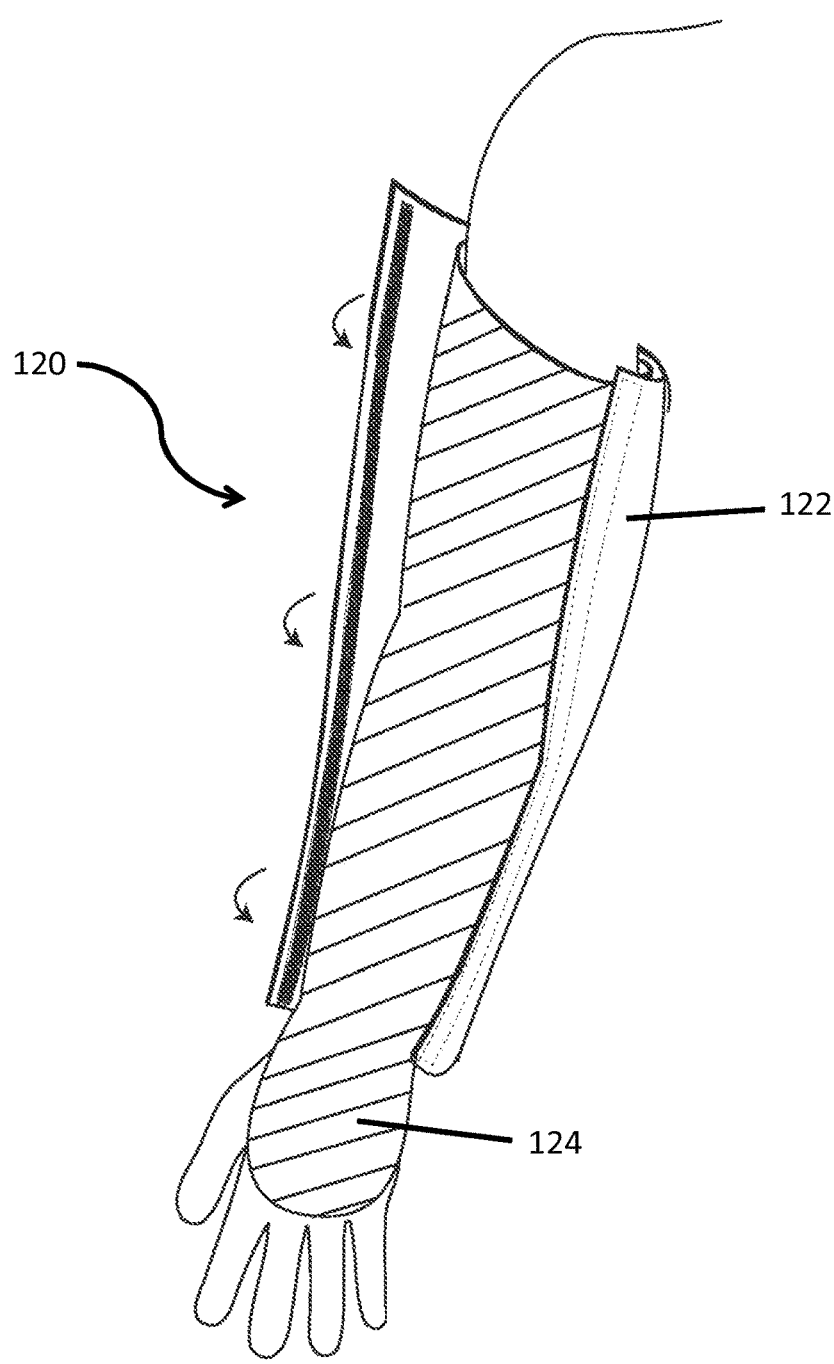
FIG. 21 illustrates a front perspective view of an embodiment of a full arm foam compression wrap of the present invention.

FIG. 1 illustrates a front perspective view of an embodiment of a full leg foam compression wrap 100 of the present invention. The wrap 100 includes a back panel 102 and a front panel 104 that may be joined around the leg. FIGS. 2A and 2B illustrate the outside 102A and inside 102B, respectively of the back panel 102 and FIGS. 3A and 3B illustrate the outside 104A and inside 104B, respectively of the front panel 104. Each panel is cut from open cell foam. The outside of the back panel 102 may be covered with a fabric 106 that has preferably been heat fused onto the foam 102. Although the fabric 106 may be glued onto the surface of the foam 102, heat fusing eliminates the use of chemical adhesive and their adverse residual effects. In addition to providing an attractive appearance, the fabric, when stretched over the foam, also provides some compression to the wrap 100, as indicated by the double arrow CA'. Hook closure material 108, such as from Velcro™ hook-and-loop material, may be sewn or otherwise secured to the side edges of the inside surface 102B of the back panel 102. A loop material 110 may be secured, again such as by sewing or heat fusing, to the outside 104A of the front panel 104. The front panel 104 is wrapped around the front of the patient's leg. Then, the back panel 102 is wrapped around the back of the leg and secured to the front panel 102 by pressing the hook material 108 to the loop material 110 on the front surface 104A of the front panel 104. Preferably, the front panel 104 has a slit 112 cut near the lower end to permit the front panel 104 to bend forward at the patient's ankle (see also FIG. 1). As will be described below, a base layer sleeve 500 (FIG. 17) is put on over the leg before the foam panels 102, 104 are put in place and a short stretch wrap material 400 (FIGS. 13-16) is wrapped around the outside of the foam panels 102, 104 to secure them in place and, more importantly, to provide the desired compression necessary to move fluid from the lower part of the leg (or the outer extremity of the limb) towards the body. FIG. 21 illustrates a front perspective view of an embodiment of a full arm foam compression wrap 120 of the present invention with foam back and front panels 122, 124, respectively, similar in construction to the full leg foam compression wrap 100.

Figures 5A, 5B:
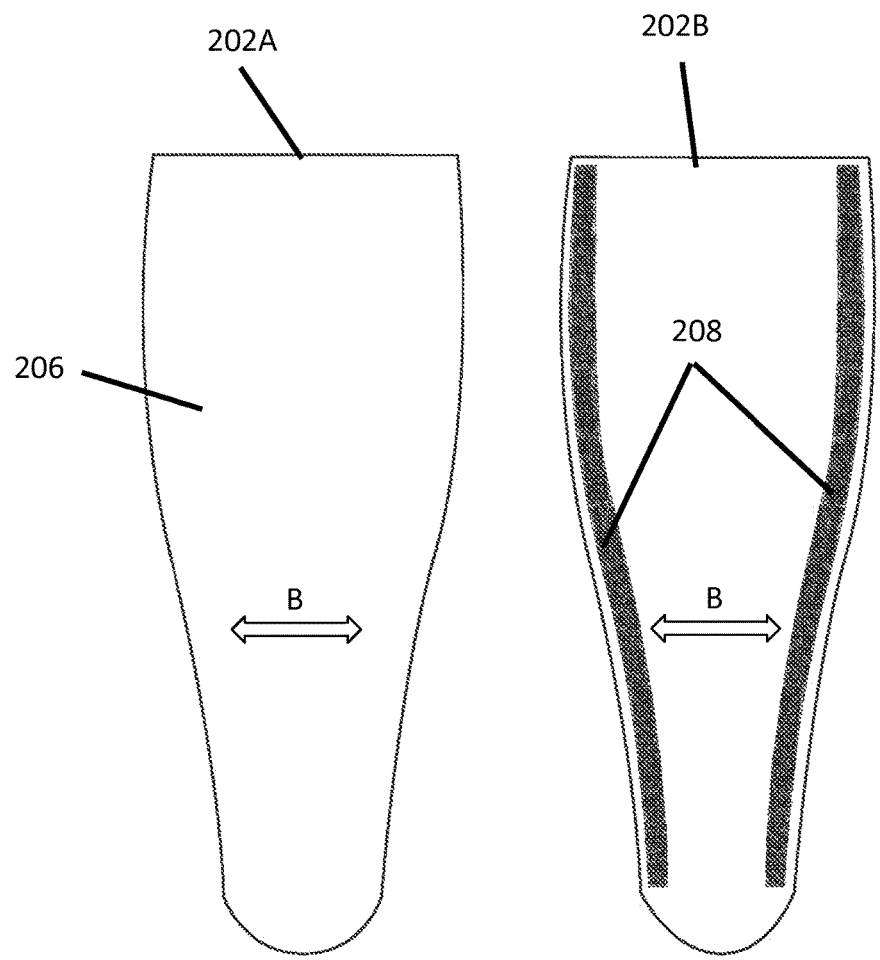
FIG. 5A illustrates the outside of the back panel of the lower leg foam compression wrap of FIG. 4.
FIG. 5B illustrates the inside of the back panel of the lower leg foam compression wrap of FIG. 4.
Figure 7:
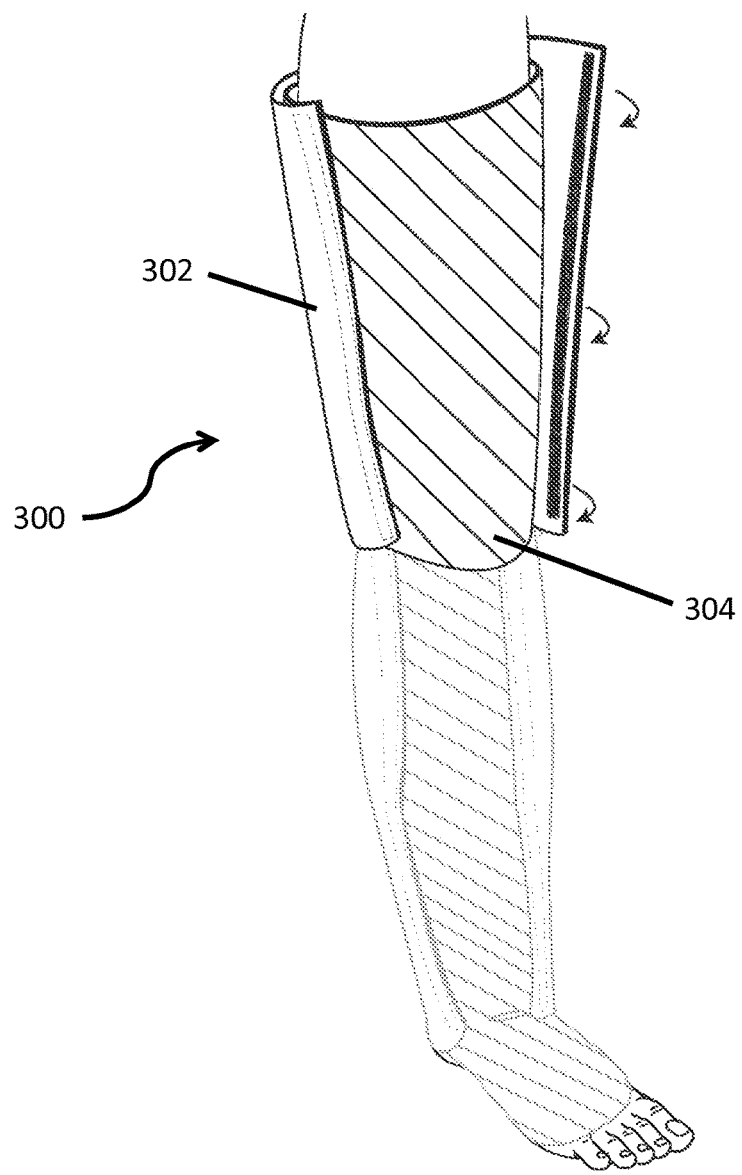
FIG. 7 illustrates a front perspective view of an embodiment of a thigh foam compression wrap of the present invention.

FIGS. 4, 5A, 5B, 6A, and 6B illustrate views of a lower leg compression wrap 200 that correspond to the views of the full leg compression wrap of FIGS. 1, 2A, 2B, 3A, and 3B, respectively. The wrap 200 includes a foam back panel 202 and a foam front panel 204 that may be joined around the lower leg, below the patient's knee. FIGS. 5A and 5B illustrate the outside 202A and inside 202B, respectively of the back panel 202 and FIGS. 6A and 6B illustrate the outside 204A and inside 204B, respectively of the front panel 204. The outside of the back panel 202 may be covered with a fabric 206 that has preferably been heat fused onto the foam 202. The fabric, when stretched over the foam, provides some compression to the wrap 200, as indicated by the double arrow 'B'. Hook closure material 208 may be sewn or otherwise secured to the side edges of the inside surface 202B of the back panel 202. A loop material 210 may be secured to the outside 204A of the front panel 204. The front panel 204 is wrapped around the front of the patient's lower leg. Then, the back panel 202 is wrapped around the back of the leg and secured to the front panel 202 by pressing the hook material 208 to the loop material 210 on the front surface 204A of the front panel 204. Preferably, a slit 212 may be cut through the front panel 204 near the lower end to permit the front panel 204 to bend forward at the patient's ankle (see also FIG. 4). A base layer sleeve 500 (FIG. 17) may be put on over the lower leg before the foam panels 202, 204 are put in place and a short stretch wrap material 400 (FIGS. 13-16) is wrapped around the outside of the foam panels 202, 204 to secure them in place and to provide the desired compression.

Figures 8A, 8B:
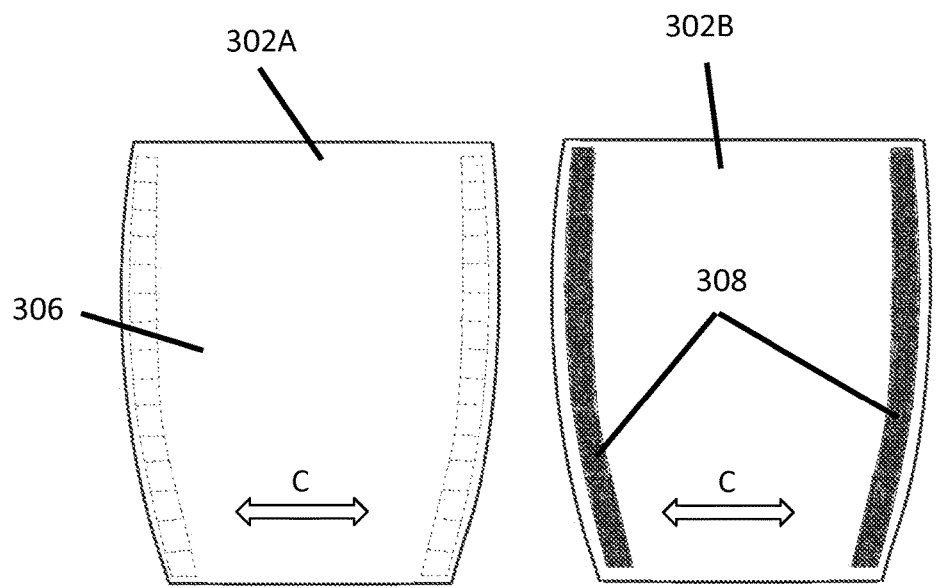
FIG. 8A illustrates the outside of the back panel of the thigh foam compression wrap of FIG. 7.
FIG. 8B illustrates the inside of the back panel of the thigh foam compression wrap of FIG. 7.
Figures 9A, 9B:
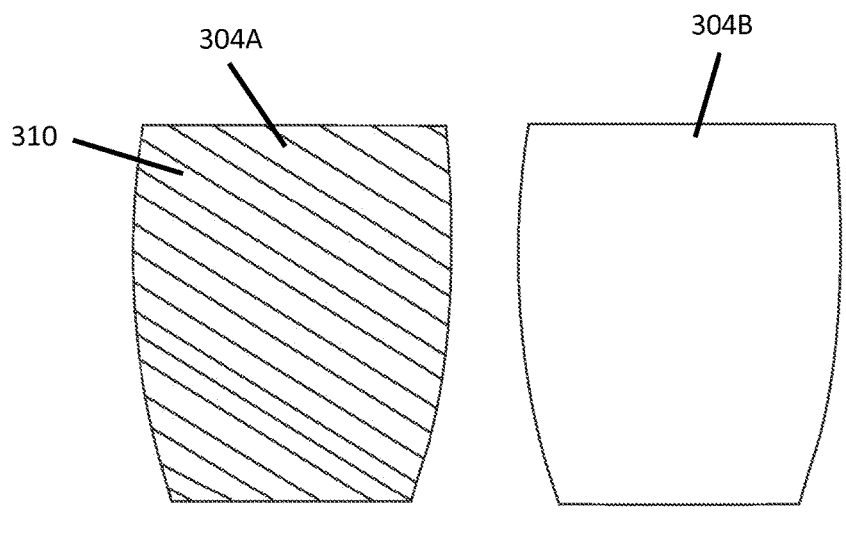
FIG. 9A illustrates the outside of the front panel of the thigh foam compression wrap of FIG. 7.
FIG. 9B illustrates the inside of the front panel of the thigh foam compression wrap of FIG. 7.

FIGS. 7, 8A, 8B, 9A, and 9B illustrate views of a thigh or upper leg compression wrap 300 that correspond to the views of the full leg compression wrap of FIGS. 1, 2A, 2B, 3A, and 3B, respectively. The wrap 300 includes a foam back panel 302 and a foam front panel 304 that may be joined around the thigh, above the patient's knee. FIGS. 8A and 8B illustrate the outside 302A and inside 302B, respectively of the back panel 302 and FIGS. 9A and 9B illustrate the outside 304A and inside 304B, respectively of the front panel 304. The outside of the back panel 302 may be covered with a fabric 306 that has preferably been heat fused onto the foam 302. Hook closure material 308 may be sewn or otherwise secured to the side edges of the inside surface 302B of the back panel 302. A loop material 310 may be secured to the outside 304A of the front panel 304. The fabric, when stretched over the foam, provides some compression to the wrap 200, as indicated by the double arrow 'C'. The front panel 304 is wrapped around the front of the patient's thigh. Then, the back panel 302 is wrapped around the back of the thigh and secured to the front panel 302 by pressing the hook material 308 to the loop material 310 on the front surface 304A of the front panel 304. A base layer sleeve 500 (FIG. 17) may be put on over the upper leg before the foam panels 302, 304 are put in place and a short stretch wrap material 400 (FIGS. 13-16) is wrapped around the outside of the foam panels 302, 304 to secure them in place and to provide the desired compression. In one embodiment, the front foam thigh panel 304 extends down and over the front foam lower panel 204 to provide full coverage of the leg (when a full leg wrap 100 is not used). The bottom of the thigh front panel 304 may be secured to the top of the of lower panel 204 with, for example, hook-and-loop material.

Figure 10:
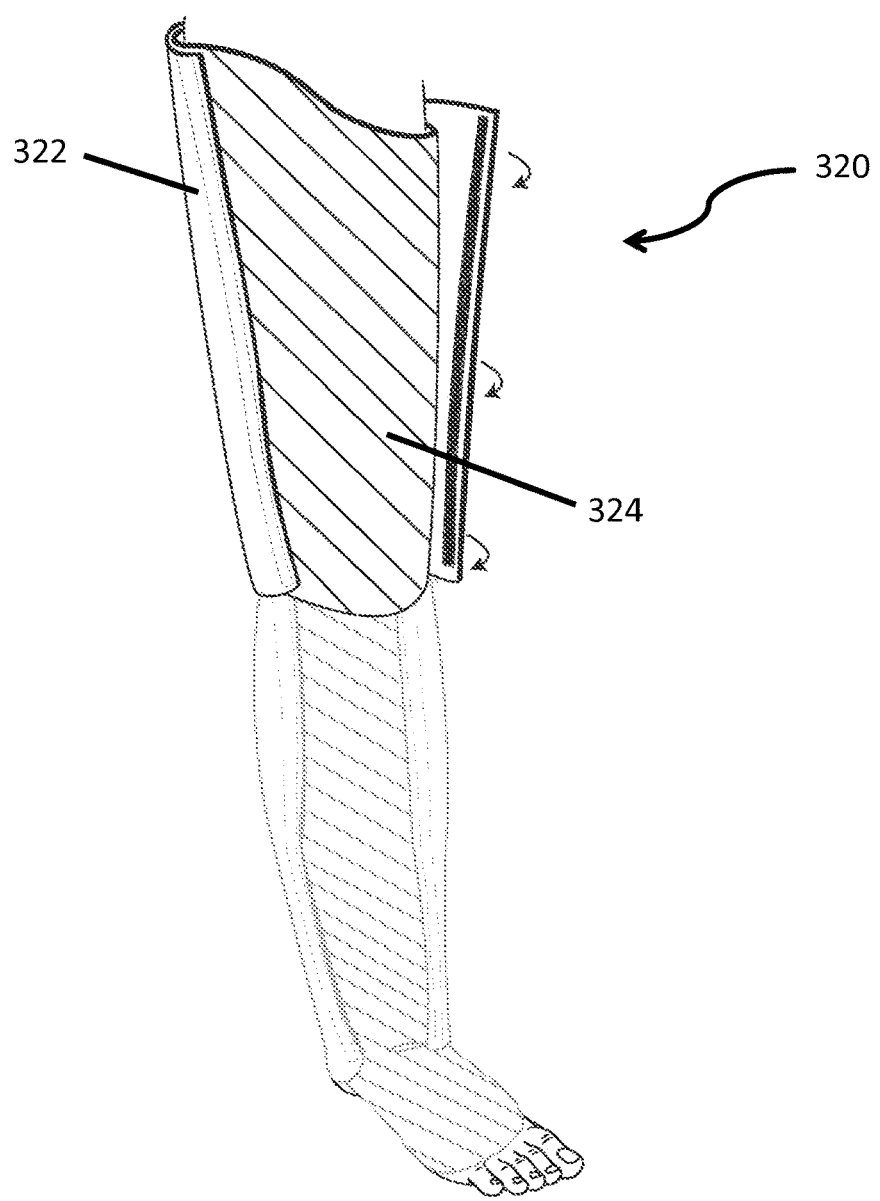
FIG. 10 illustrates an alternative embodiment of a thigh or upper leg compression wrap.
Figures 11, 12:
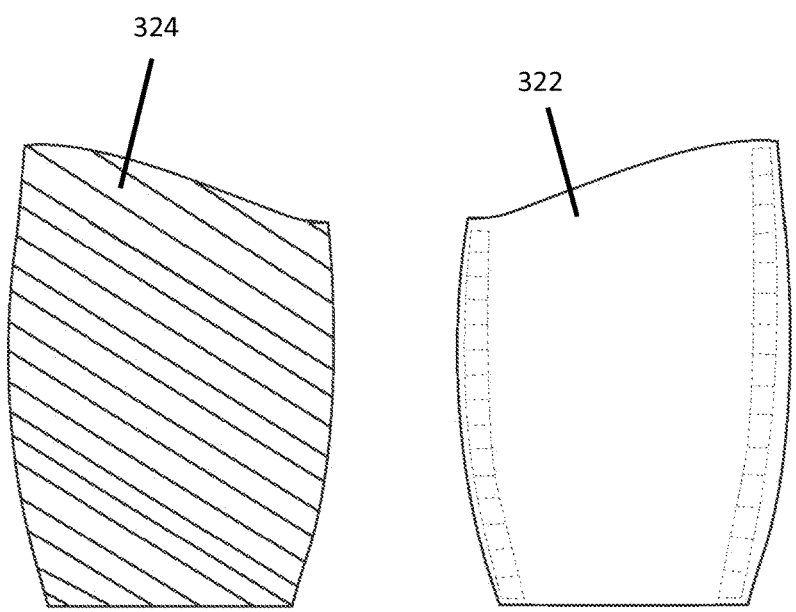
FIG. 11 illustrates the outside of the front panel of the thigh foam compression wrap of FIG. 10.
FIG. 12 illustrates the outside of the back panel of the thigh foam compression wrap of FIG. 10.

FIG. 10 illustrates an alternative shape for a thigh or upper leg compression wrap 320. The wrap 320 includes a foam back panel 322 and a foam front panel 324 that are with on a diagonal along the top edges, as more clearly shown in FIGS. 11 and 12, to provide more comfort along the patient's inner thigh. The back and front panels 322, 324 of the compression wrap 320 wrap around the upper leg and attach to each other in the same manner as the embodiment of the upper leg compression wrap of FIGS. 7, 8A, 8B, 9A, and 9B.

The dimensions of each foam panel will depend on the size, age, and needs of the patient. Each foam panel may be custom cut for each patient or may be provided in a number of precut common sizes. The foam may be any thickness, again depending on the individual patient; ¼", ⅜", ½", and ⅜" are useful thicknesses. The foam panels are preferably cut from open cell foam.

Figure 13:
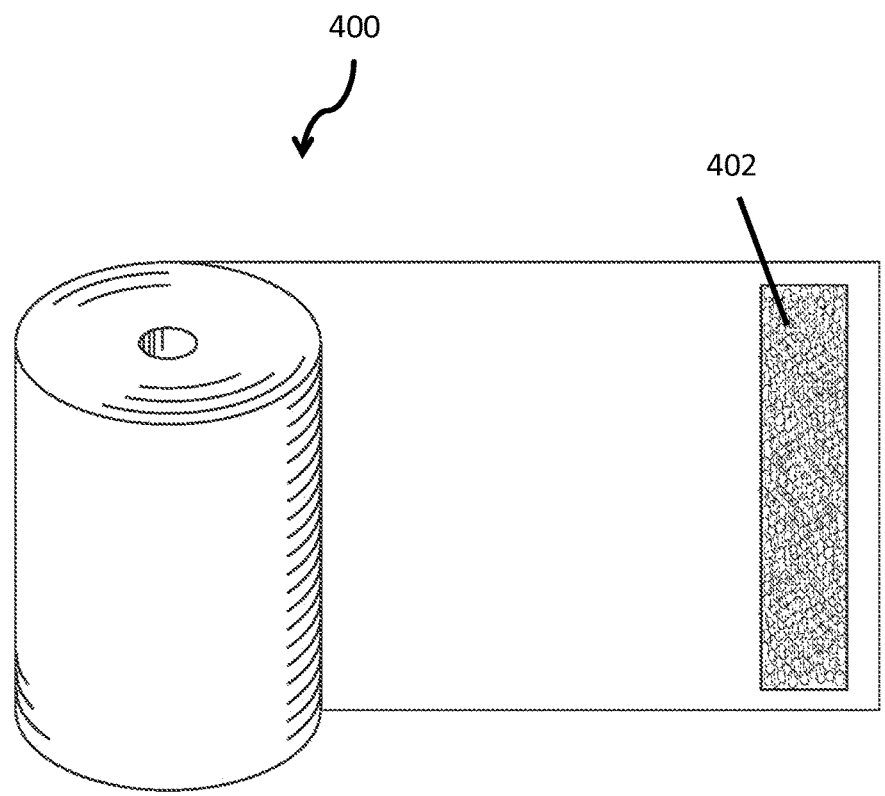
FIG. 13 illustrates an embodiment of a roll of short stretch wrap of the present invention.
Figure 14:
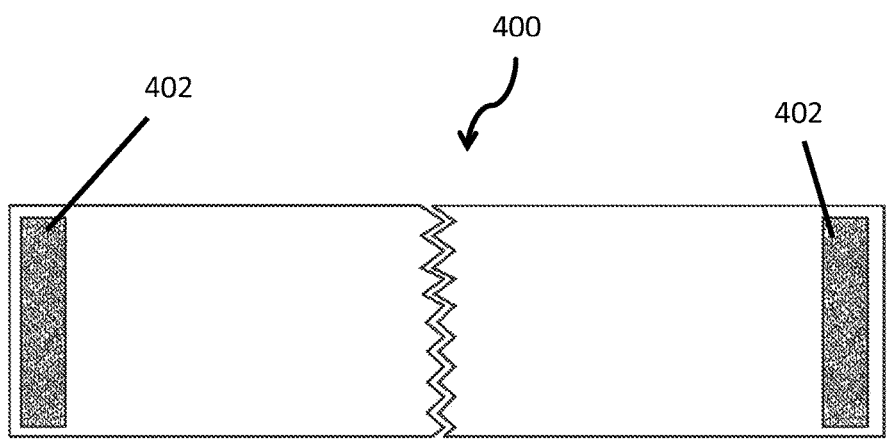
FIG. 14 illustrates the inside of the ends of the short stretch wrap of FIG. 13.
Figure 15:
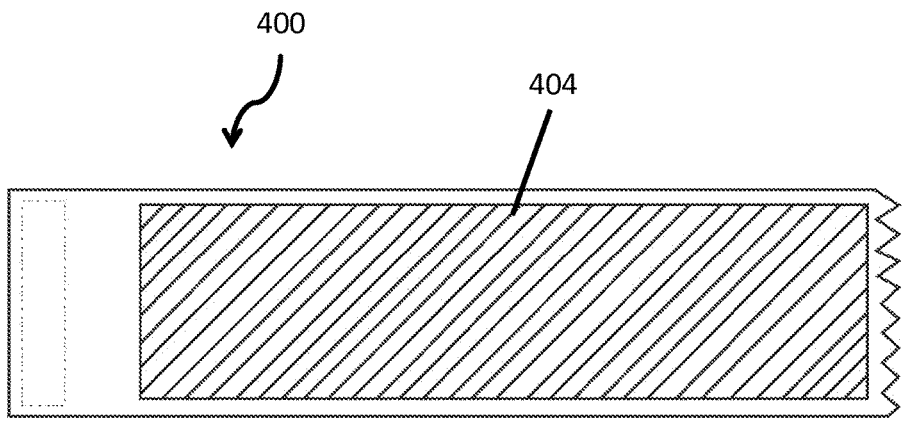
FIG. 15 illustrates the outside of an end of the short stretch wrap of FIG. 13.
Figure 16:
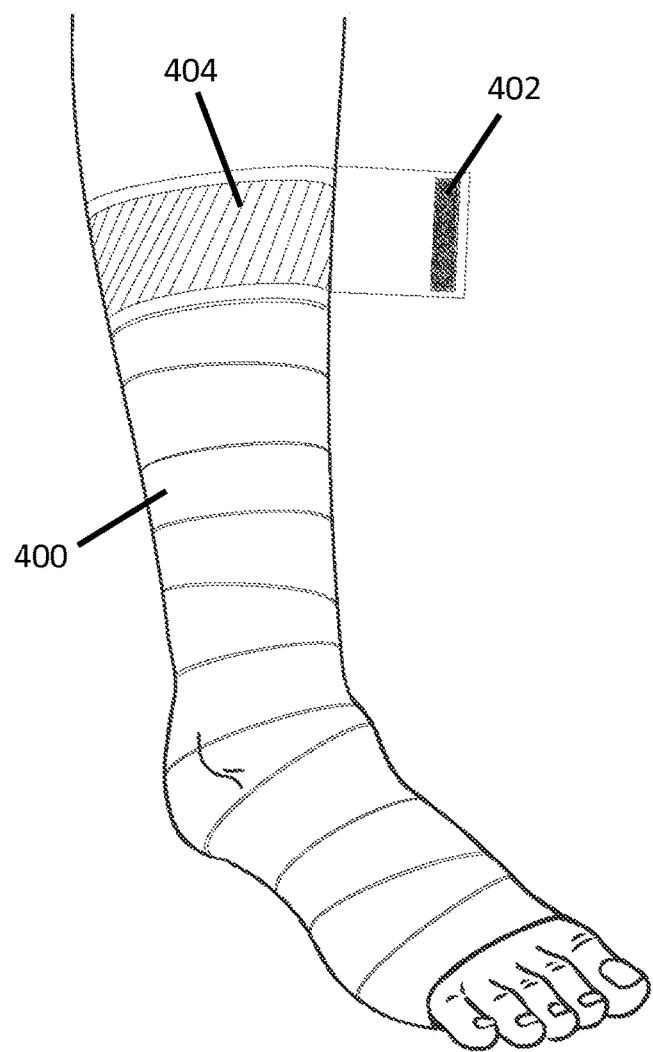
FIG. 16 illustrates the short stretch wrap of FIG. 13 in place around the lower leg compression wrap of FIG. 4.

As briefly noted above, the compression foam panels may be wrapped with short stretch wrap. FIG. 13 illustrates a roll 400 of such wrap. The wrap 400 may be provided in a variety of lengths and widths. Preferably, hook closure fabric is secured, such as by sewing, to one side (the side that will become the inside of the wrap 400) of each end of the wrap 400 (see also FIG. 14). Loop closure fabric 404 is secured, such as by sewing to reduce any loss of stretchability of the wrap 400, along a length of the opposite side (the side that will become the outside of the wrap 400) near the ends of the wrap 400 (see FIG. 15). When the panels are wrapped with multiple rolls of short stretch wrap 400, the hook material 402 of one roll may be used to secure the beginning end of the roll to the loop material 404 at the end of the previous roll. Hook material 402 at the end of the last roll may be used to secured the end to the loop material 404 at the same end, thus securing the wrap (see FIG. 16). No clips, tape, or other means are necessary, making it easier to the patient to self wrap, even with one hand. Furthermore, the foam panels may be wrapped with different amounts of compression along different parts of the limb, either by wrapping with less compression as the wrapping progresses from the extremity of the limb towards the body or by separately wrapping different portions of the limb with different short stretch rolls 400 and applying different amounts of compression to each. As fluid is moved by the compression towards the body, swelling of the limb will decrease, causing the wrap to loosen. It becomes easy to the patient to quickly unwrap the short stretch wraps 400 and re-wrap them to maintain the desired compression on the limb and keep the fluid moving towards the body. Additionally, the foam panels may also be tightened at the same time to remove the resulting space between the limb and the inside of the panels, thereby maintaining the proper compression. And, as swelling in the limb is reduced over time, the patient may trim the back foam thigh panels 304 along sides from the top down to reduce the width and trim the length or width, or both, of the lower leg foam panels 204, thereby aiding the maintenance of the reduced swelling. Similarly, the width of the full length wrap may also be trimmed.

Figures 19, 20:
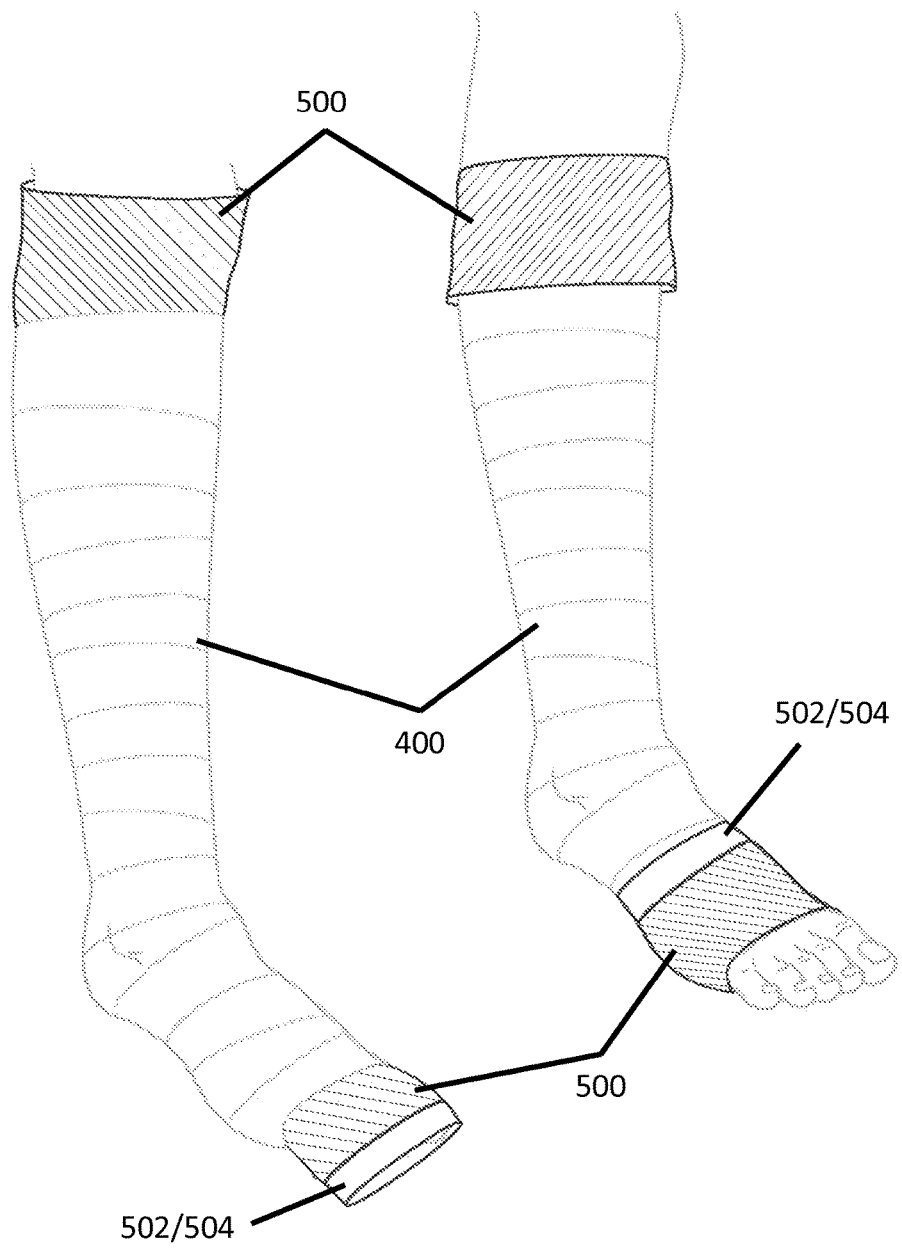
FIG. 19 illustrates the ends of the inner sleeve of FIG. 14 after the lower leg foam compression wrap of FIG. 4 has been put secured on a leg with the short stretch wrap of FIG. 13.
FIG. 20 illustrates the ends of the inner sleeve of FIG. 17 after being folded over the ends of the foam compression wrap of FIG. 4 and short stretch wrap of FIG. 13.

As also briefly noted above, the patient preferably puts on a base layer sleeve 500 (see FIG. 17) before putting the foam panels in place. The sleeve 500 is preferably made from a moisture wicking fabric. As with the foam panels, the sleeve 500 may be custom made for each patient or may be provided in a number of common lengths and diameters. The sleeve 500 may be cut as a trapezoid from a roll of appropriate material. The outer edges may then be sewn together to form a tapering sleeve 500. As illustrated in FIG. 18, a band of elastic 502 may be sewn around at least the lower end of the sleeve, such as by sewing the elastic 502 into a pocket 504 around the end. Preferably, the sleeve 500 is cut several inches longer than the length of the limb to be covered (FIG. 19) so that the excess at the ends may be folded over the upper and lower ends of the short stretch wrap 400 (FIG. 20).

The description of the present invention has been presented for purposes of illustration and description, but is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A therapeutic compression wrap, comprising:
   a first front foam panel having inside and outside surfaces and configured to cover a front portion of at least part of a patient's limb;
   loop closure material stretched over and secured to the outside surface of the first front foam panel;
   a first back foam panel, separate from the first front foam panel, having inside and outside surfaces and configured to cover a back portion of the at least part of the limb;
   fabric stretched over and secured to the outside surface of the first back foam panel; and
   first hook closure material secured to side edges of the inside surface of the back foam panel, the first hook closure material matable with the loop closure material of the first front foam panel, whereby side edges of the back foam panel are securable to the front foam panel and whereby the first front and back foam panels encircle the limb from a bottom of the first front and back foam panels to a top of the first front and back foam panels.

2. The compression wrap of claim 1, wherein the fabric is heat fused onto the outside surface of the first back foam panel and the loop closure material is heat fused to the outside surface of the first front foam panel.

3. The compression wrap of claim 1, wherein the first front foam panel is configured to cover only the front portion of the patient's lower leg below the knee and the first back foam panel is configured to cover only the back portion of the patient's lower leg below the knee.

4. The compression wrap of claim 3, wherein a second front foam panel, separate from the first front foam panel, is configured to cover the front portion of the patient's upper leg and a second back foam panel, separate from the first back foam panel and separate from the second front foam panel, is configured to cover the back portion of the patient's upper leg.

5. The compression wrap of claim 4, wherein:
   the second front foam panel is configured to cover the front portion of the patient's upper leg and knee[and the second back foam panel is configured to cover the back portion of the patient's upper leg]; and
   the compression wrap further comprises second hook material along the inside surface of a lower edge of the second front foam panel, the hook material matable with the loop closure material on the outside surface of the first front foam panel.

6. The compression wrap of claim 1, wherein the first front foam panel is configured to cover the front portion of the patient's upper leg and the first back foam panel is configured to cover the back portion of the patient's upper leg.

7. The compression wrap of claim 1, wherein the first front foam panel is configured to cover the front portion of the patient's arm and the first back foam panel is configured to cover the back portion of the patient's arm.

8. The compression wrap of claim 1, further comprising an inner sleeve configured to receive the patient's limb under the first front and back foam panels.

9. The compression wrap of claim 8, further comprising a band of elastic around at least one opening of the inner sleeve.

10. The compression wrap of claim 1, further comprising:
at least one roll of short stretch wrap having first and second ends wrappable around the first front and back foam panels from the bottom to the top of the first front and back foam panels;
third hook material on a first surface of the first and second ends; and
loop material along a second surface of the first and second ends mateable with the third hook material whereby the first front and back foam panels are enclosed with compression within the at least one roll of short stretch wrap.

11. A method of applying a compression wrap to a patient's limb, comprising:
pulling an inner sleeve over at least part of the patient's limb;
covering a front portion of at least part of the limb with a first front foam panel, the first front foam panel having first loop closure material stretched over and secured to an outside surface;
covering a back portion of the at least part of the limb with a first back foam panel, the first back foam panel separate from the first front foam panel and having fabric stretched over and secured to an outside surface and further having first hook closure material secured to side edges of an inside surface;
mating the first hook closure material of the first back foam panel to the first loop closure material of the first front foam panel, whereby the at least part of the limb is enclosed within the first front and back foam panels; and
wrapping at least one roll of short stretch wrap around the first front and back foam panels, the at least one roll of short stretch wrap having second hook closure material on a first surface of an end and further having second loop closure material along a second surface of the end; and
mating the second hook closure material to the second loop closure material, whereby the first front and back foam panels are enclosed with compression within the at least one roll of short stretch wrap.

12. The method of claim 11, wherein:
covering a front portion of at least part of the limb with a first front foam panel comprises:
covering the front portion of the patient's lower leg with the first front foam panel; and
covering the front portion of the patient's upper leg and knee with a second front foam panel;
covering a back portion of the at least part of the limb comprises:
covering the back portion of the patient's lower leg with the first back foam panel; and
covering the back portion of the patient's upper leg with a second back foam panel;
the method further comprising mating second hook material along the inside surface of a lower edge of the second front foam panel with the first loop closure material on the outside surface of the first front foam panel.

13. The method of claim 11, wherein:
covering a front portion of at least part of the limb with a first front foam panel comprises covering the front portion of the patient's arm with the first front foam panel; and
covering a back portion of the at least part of the limb comprises covering the back portion of the patient's arm with the first back foam panel.

14. A method of providing a therapeutic compression wrap, comprising:
cutting a first front foam panel having inside and outside surfaces to cover a front portion of at least part of a patient's limb;
stretching and securing loop closure material to the outside surface of the first front foam panel;
cutting a first back foam panel, separate from the first front foam panel, having inside and outside surfaces to cover a back portion of the at least part of the limb;
stretching and securing fabric to the outside surface of the first back foam panel; and
securing first hook closure material to side edges of the inside surface of the back foam panel, the first hook closure material matable with the loop closure material whereby the back foam panel is securable to the front foam panel.

15. The method of claim 14, wherein:
securing the loop closure material to the outside surface of the first front panel comprises heat fusing the loop closure material to the outside surface of the first front panel; and
securing the fabric to the outside surface of the first back panel comprises heat fusing the fabric to the outside surface of the first back panel.

16. The method of claim 14, further comprising providing an inner sleeve configured to receive the patient's limb before the front and back portions of the patient's limb are covered by the first front and back foam panels.

17. The method of claim 14, further comprising:
providing a roll of short stretch wrap having first and second ends;
securing second hook material to a first surface of the first and second ends; and
securing loop material along a second surface of the first and second ends.

* * * * *